(12) United States Patent
Zunke, Jr. et al.

(10) Patent No.: US 11,636,781 B2
(45) Date of Patent: Apr. 25, 2023

(54) URETHRA AND PROSTATE MODEL AND METHOD OF USE

(71) Applicant: Teleflex Life Sciences Limited, Valletta (MT)

(72) Inventors: Dale N. Zunke, Jr., Smyrna, GA (US); Ronda M. Heiser, San Jose, CA (US); Lynda Angela Murillo, Anaheim, CA (US)

(73) Assignee: Teleflex Life Sciences Limited, Valletta (MT)

( * ) Notice: Subject to any disclaimer, the term of this patent is extended or adjusted under 35 U.S.C. 154(b) by 1070 days.

(21) Appl. No.: 16/360,383

(22) Filed: Mar. 21, 2019

(65) Prior Publication Data

US 2019/0295444 A1    Sep. 26, 2019

Related U.S. Application Data

(60) Provisional application No. 62/646,741, filed on Mar. 22, 2018.

(51) Int. Cl.
*G09B 23/30*  (2006.01)
*G09B 23/28*  (2006.01)
*B33Y 10/00*  (2015.01)
*A61B 17/24*  (2006.01)
*B29C 45/14*  (2006.01)

(52) U.S. Cl.
CPC .......... *G09B 23/30* (2013.01); *G09B 23/285* (2013.01); *A61B 17/24* (2013.01); *B29C 45/14* (2013.01); *B33Y 10/00* (2014.12)

(58) Field of Classification Search
CPC ...... G09B 23/30; G09B 23/285; A61B 17/24; B29C 45/14; B33Y 10/00; B33Y 80/00
See application file for complete search history.

(56) References Cited

U.S. PATENT DOCUMENTS 7,648,367 B1    1/2010  Makower et al.
2018/0240366 A1 *  8/2018  Felsinger ............... G09B 23/30

FOREIGN PATENT DOCUMENTS

CN    201417552 Y  *  3/2010
CN    112885217 A  *  6/2021  ............. G09B 23/28

* cited by examiner

*Primary Examiner* — Jeffrey S Vanderveen
(74) *Attorney, Agent, or Firm* — Kenneth E. Levitt; Erik T. Nyre

(57) ABSTRACT

A device and method for education and practice of transurethral entry into and manipulation of the prostate by various instruments that prevent, or at least reduce, unwanted contact and damage to surrounding structures.

20 Claims, 9 Drawing Sheets

URETHRA AND PROSTATE MODEL AND METHOD OF USE

BACKGROUND OF THE INVENTION

This application claims priority to and the benefit of U.S. Provisional Application No. 62/646,741 filed Mar. 22, 2018, entitled "Urethra and Prostate Model and Method of Use," which is incorporated herein by reference in its entirety

BACKGROUND OF THE INVENTION

The present invention relates generally to medical education tools, and more particularly to anatomical models and associated methods of use for practicing medical procedures.

Anatomical models adapted for use in surgical or procedural training allow physicians to practice at least some aspects of a procedure using the model rather than a cadaver, living animal, or human patient. Anatomical models can also facilitate research and development of new devices, treatments, and procedures.

One medical field that can benefit from such anatomical models is urology, as patient treatment often requires scope-guided procedures and surgeries of the male and female urinary-tract system and the male reproductive organs. In men, surgical intervention often involves manipulation, resizing, and/or at least partial removal of prostate tissue to treat Benign Prostatic Hyperplasia (BPH), a condition characterized by noncancerous enlargement of the prostate.

Procedures for treating BPH include Transurethral Resection of the Prostate, Transurethral Electrovaporization of Prostate, Transurethral Incision of the Prostate, Transurethral Microwave Thermotherapy, Transurethral Needle Ablation and other interventional procedures that focus on destruction of prostatic tissue.

Common to all of these procedures is the insertion of instruments through the urethra to access and manipulate the prostate. The present disclosure relates to an anatomical model and method of use to practice transurethral entry of an instrument into the prostate and subsequent use of the instrument to displace, compress, penetrate and/or resect the prostate.

SUMMARY OF THE INVENTION

Embodiments of the present invention are directed towards a device and method for practicing medical procedures relating to the urethra and prostate. The device includes an anatomical model of a human urethra and prostate, a holder, and a template.

The template defines various positions and angles for insertion, manipulation, and withdrawal of an instrument. The various positions and angles are indicated to prevent or minimize unwanted contact with and potential damage to surrounding tissue and anatomical structures.

In a particular embodiment, the template includes an indication to simulate unwanted contact by an instrument with a bone-like structure and/or an indication to simulate incomplete deployment of an implant.

Various embodiments of the anatomical model and holder are disclosed and described herein. Moreover, various ways in which the structures of the anatomical model can be altered by an instrument are discussed.

Other features and advantages of embodiments of the present invention will become apparent from the following description, taken in conjunction with the accompanying drawings, which illustrate, by way of example, certain principles of the invention.

DETAILED DESCRIPTION OF ILLUSTRATIVE EMBODIMENTS

Figure 1:
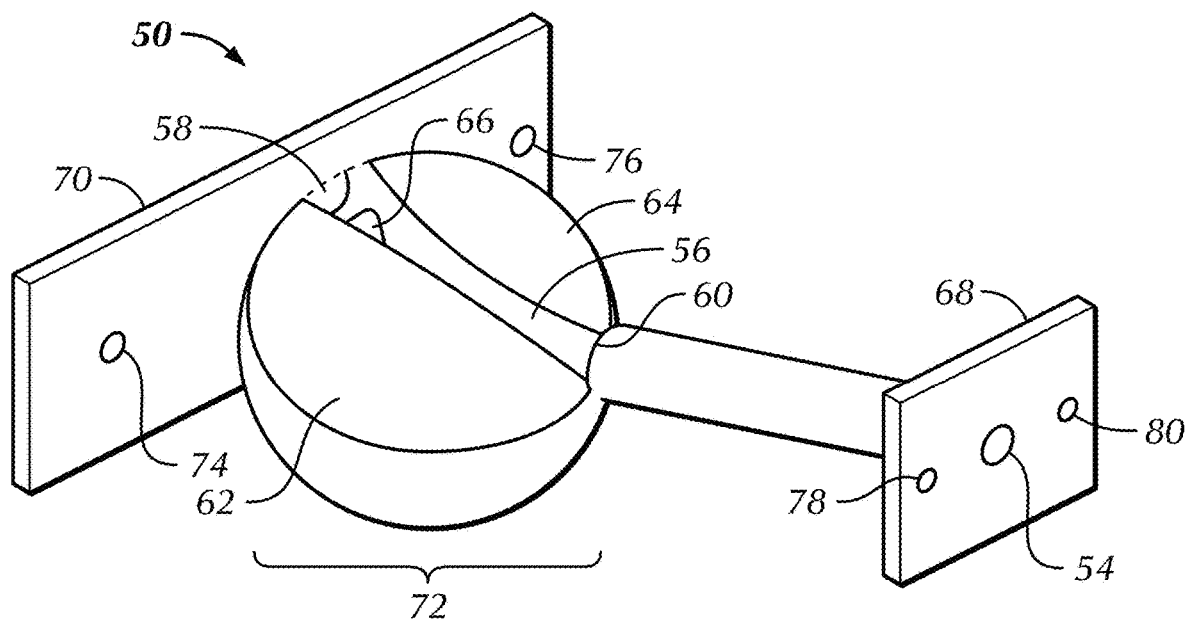
FIG. 1 is a perspective view of an anatomical model representing a human prostate and urethra and various features thereof.
Figure 2A:
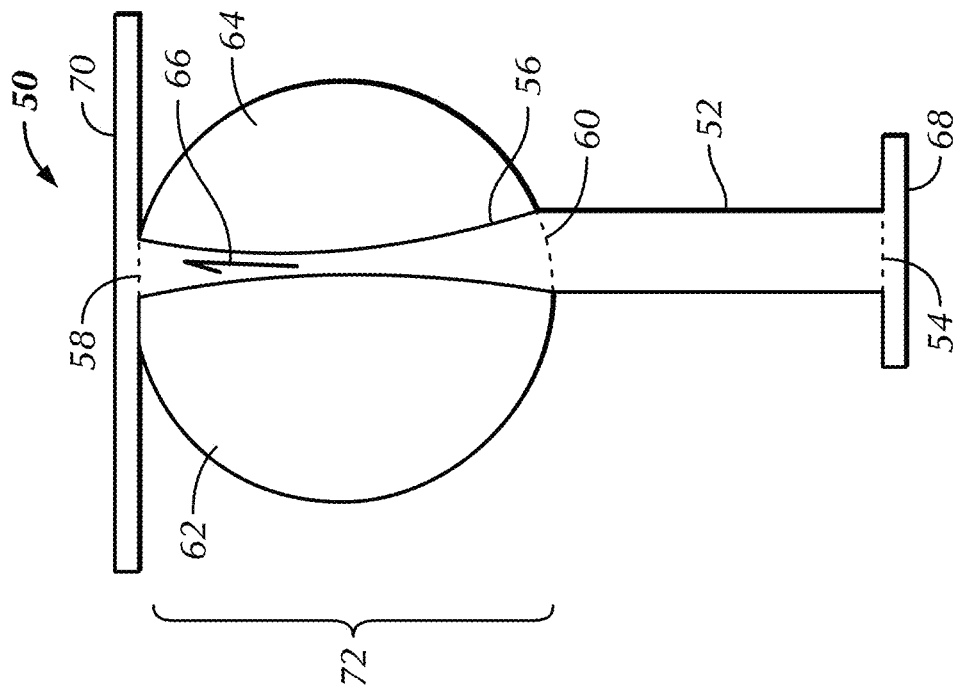
FIG. 2A is a top view of one embodiment of an anatomical model.
Figure 2B:
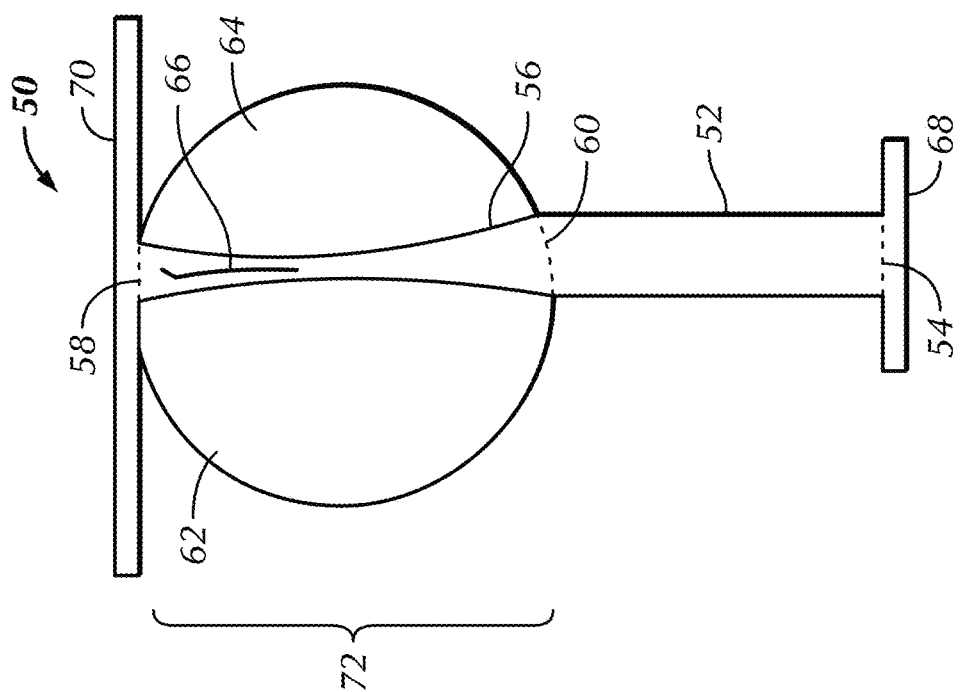
FIG. 2B is a top view of another embodiment of an anatomical model.
Figure 3:
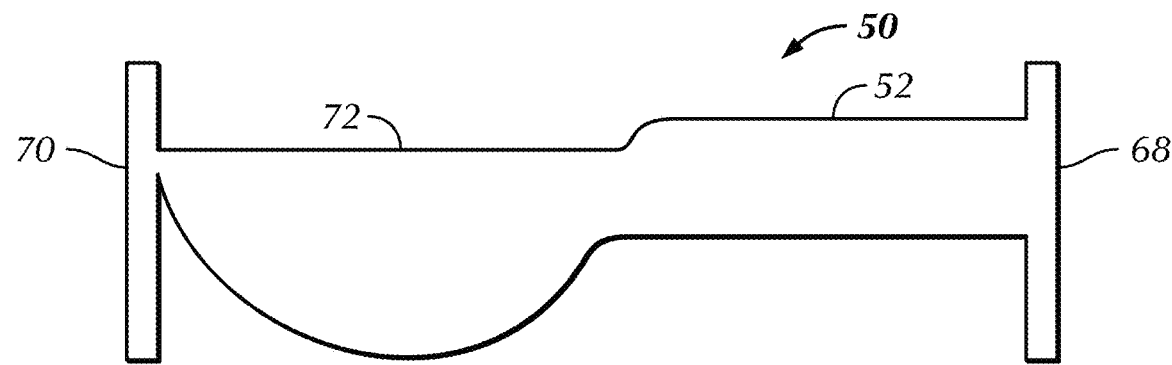
FIG. 3 is a side view of an anatomical model.
Figure 4A:
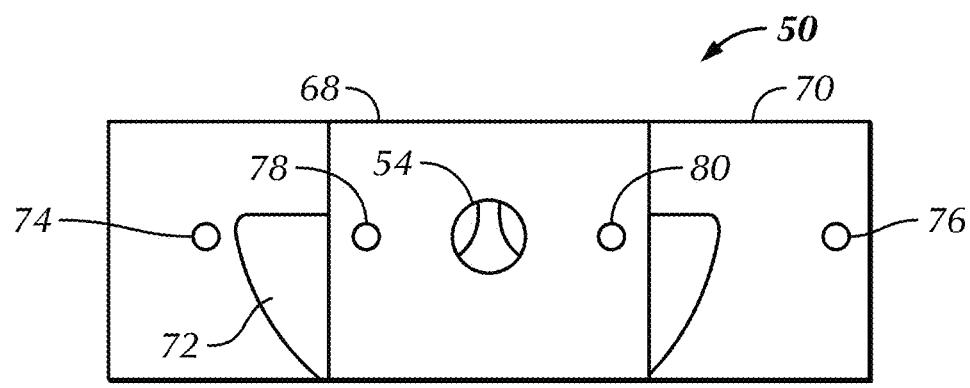
FIG. 4A is one end view of an anatomical model.
Figure 4B:
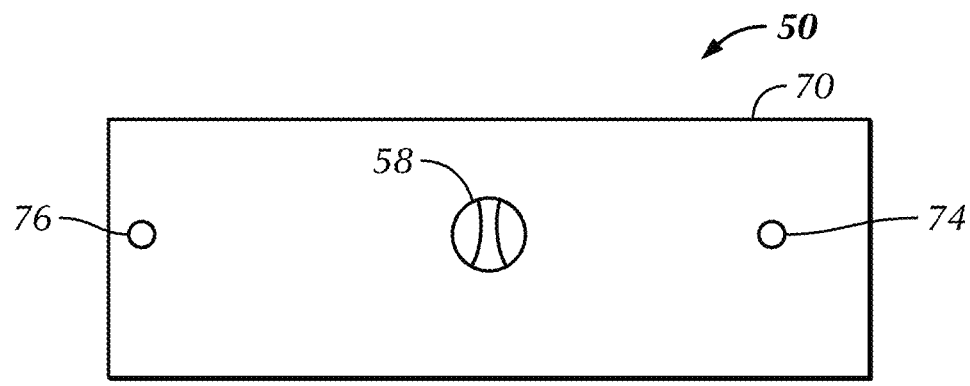
FIG. 4B is another end view of an anatomical model.
Figure 5:
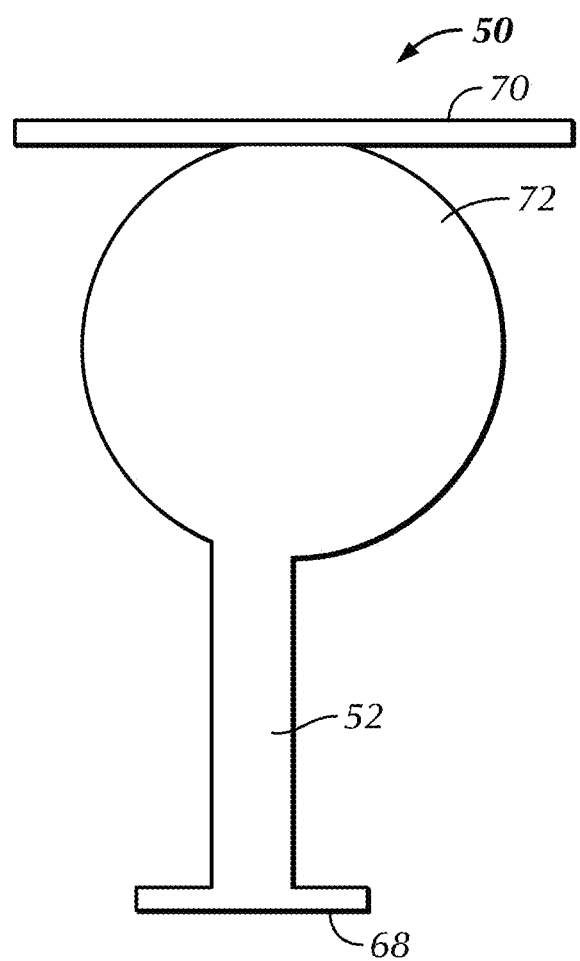
FIG. 5 is a bottom view of an anatomical model.

Turning now to the figures, which are provided by way of example and not limitation, the present disclosure is directed to a device for practicing transurethral entry into the prostate that prevents, or at least reduces, unwanted contact and damage to surrounding tissue and anatomical structures. Generally, embodiments of a device according to the present invention include an anatomical model, a holder for the model, and a template that, when aligned with the model, defines insertional and procedural angles and positions for an instrument into the model.

FIGS. 1-5 illustrate various views of model 50, which represents the anatomical structure of a human urethra and prostate. Model 50 can be manufactured by conventional means, such as injection molding, 3D printing, and other comparable manufacturing methods, from various flexible materials including rubber, vinyl, thermoplastic urethane, thermoplastic elastomer, or thermoplastic vulcanizate. Generally, polymeric materials are preferred. Model 50 includes duct 52 with opening 54, and body 72 with opening 58 and opening 60 (openings in the model are indicated by dashed lines). Duct 52 encloses a lumen through which an instrument can be inserted. In some embodiments, the lumen enclosed by duct 52 is continuous with lumen 56 through opening 60. Lumen 56, which represents the prostatic urethra, resides in body 72 and is situated between two structures, lobe 62 and lobe 64, which represent lateral lobes of the prostate. Lumen 56 is partially exposed to allow visualization of the distal end of an instrument as the instrument passes through duct 52, through opening 60 and into lumen 56. Inside lumen 56 can be insert 66, which represents the median lobe of the prostate. Insert 66 can be various lengths and shapes and can be situated at different points along the length of lumen 56. Two embodiments of insert 66, differing in both shape and position within lumen 56, are shown in FIG. 2A and 2B. Insert 66 can be permanently affixed to lumen 56 or removable to simulate the anatomical variation of the presence and prominence of the median lobe in patients. Insert 66 is optional and therefore may only be present in some embodiments of the invention.

Model 50 also includes two attachment pieces configured at opposite ends of the model, attachment piece 68, which shares opening 54 with duct 52, and attachment piece 70, which shares opening 58 with body 72. Attachment piece 70 contains hole 74 and hole 76. Attachment piece 68 contains hole 78 and hole 80.

In some embodiments, components of model 50 can be removable. Such components can be inserted into or attached to model 50 by structures including, but not limited to, slots or cavities that fit a detachable element, magnetic attachments, hook and loop type fasteners, screw type fasteners, adhesives, or combinations thereof.

Figure 6:
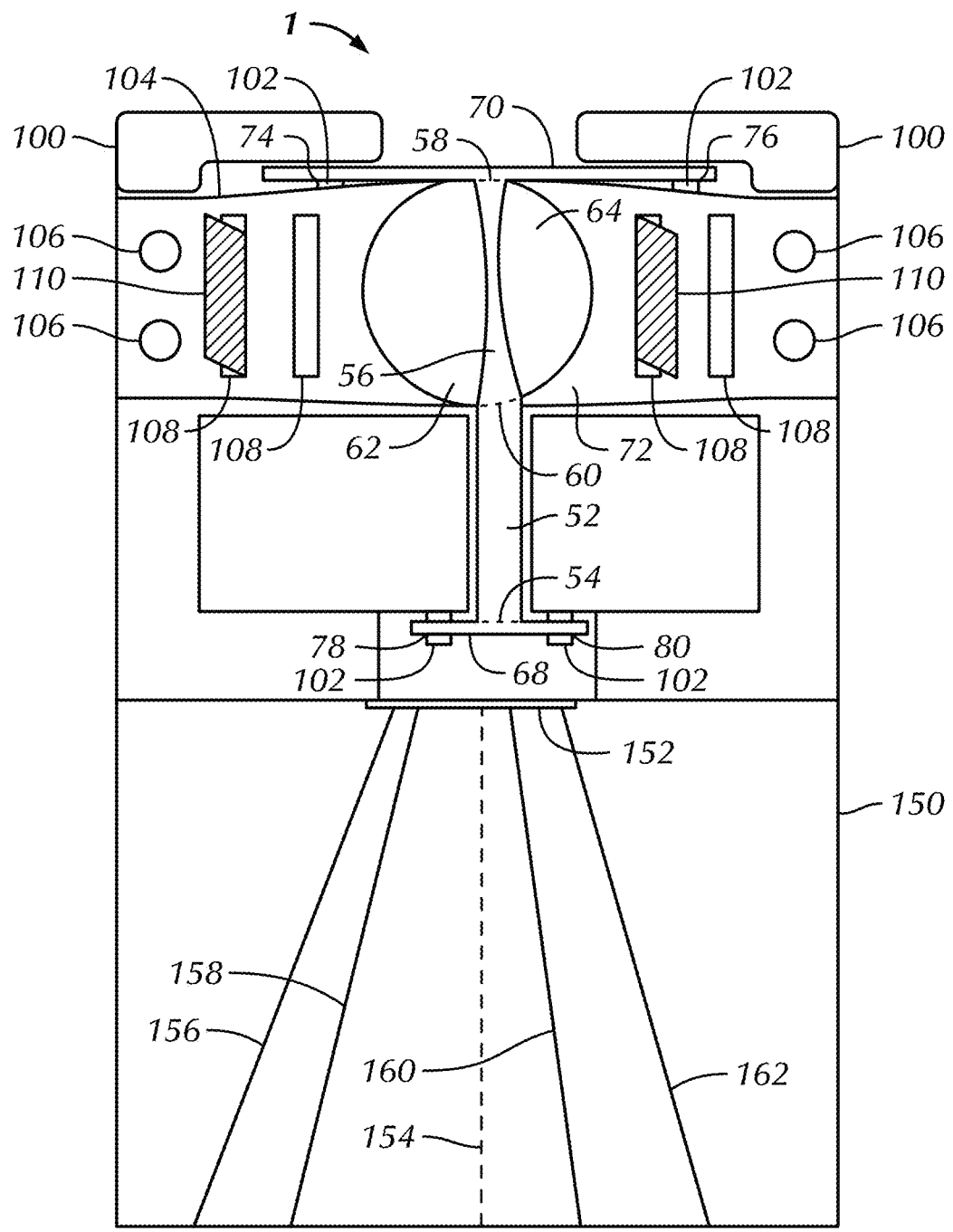
FIG. 6 is a top view of a device for practicing transurethral procedures.

The attachment pieces 68 and 70 serve to secure model 50 to holder 100 as shown in FIG. 6. Holder 100 is designed to allow access by an instrument to opening 54 and opening 58 of model 50. In some embodiments, such as those illustrated in FIG. 6, holder 100 has pegs 102 that fit through hole 74 and hole 76 of attachment piece 70 and hole 78 and hole 74 of attachment piece 68 to hold model 50 in place. Model 50 can be further secured by a cover 104 that lays over body 72. In some embodiments, cover 104 attaches to holder 100 by magnets 106. In other embodiments, cover 104 is configured to snap into place. Cover 104 can be made of a clear material such as plastic or glass.

Holder 100 can further include slots 108 that are configured to hold anatomical inserts 110. The anatomical inserts 110 represent anatomical structures around or near the anatomy represented by model 50. Such anatomical structures include bone, and thus anatomical inserts 110 can be rigid when they are intended to represent bone. The physical and mechanical nature (i.e., the relative rigidity) of anatomical inserts 110 can be chosen to represent other anatomy or implanted structures that may be around or near the anatomy represented by model 50.

Figure 7:
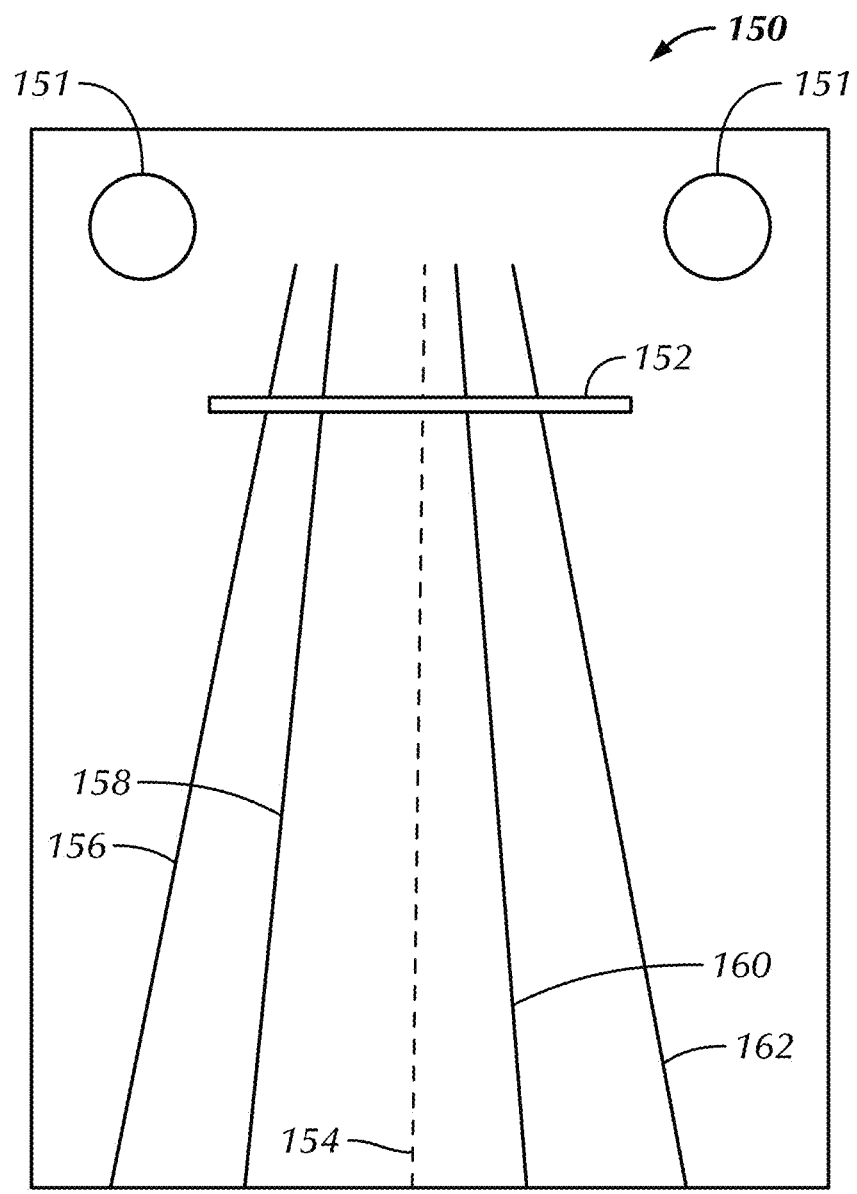
FIG. 7 is a top view of a template indicating instrument insertion and manipulation for transurethral procedures.

Template 150 of device 1 is shown in FIG. 6 and FIG. 7. Template 150 serves to physically guide a user to insert and manipulate an instrument into model 50 in such a manner that prevents unwanted contact and damage to surrounding structures. This guidance is in the form of insertional and procedural angles and positions for instrument alignment as defined by different guidelines printed on template 150. During use of device 1, template 150 is aligned with holder 100 by guideline 152. The other guidelines of template 150 indicate positions related to different procedures that can be simulated by use of device 1 and an instrument. These procedure simulation guideline markers can include "normal deployment," "bone contact," "bone contact with recovery," "incomplete anchor deployment," "incomplete suture deployment," "prostate incision simulation," and other markers or similar markers. In some embodiments, holder 100 is equipped with suction cup feet that facilitate attachment to the surface of template 150 or through template 150 to a surface below. In some embodiments, template 150 includes holes 151 that accommodate the suction cup feet on holder 100, allowing the suction cup feet to pass through template 150 and mount to the surface beneath template 150, such as a table.

According to certain embodiments of the invention, the purpose of the devices disclosed herein is to allow medical trainees to practice transurethral access of an instrument to the prostate, deploying an instrument to penetrate prostatic tissue, manipulation of an instrument inserted in the prostate, and withdrawal of an instrument from the prostate and urethra with the goal of minimizing unwanted contact with and preventing damage to surrounding structures. The simulations derived from the devices disclosed herein can prepare medical trainees for procedures they will ultimately perform on patients. For trainees or practitioners that already perform such procedures, use of the devices disclosed herein can improve their technique. Instruments used to manipulate the prostate can be inserted directly into model 50 or delivered using a sheath.

The devices disclosed herein can be used to simulate entry and navigation through different variations or conditions of the urethra and prostate. Therefore, the anatomical components of model 50 can be configured to represent normal anatomical variations, disease states or disorders, effects of pathology, pathogenic or etiological stages of a disorder, congenital malformations, anatomical anomalies, effects of prior surgery, effects of prior therapy, effects of drug administration, effects of aging or maturation, and/or combinations thereof. In some embodiments, other structures of the male reproductive system can be included in model 50. Such structures can be permanently attached or removable.

Figure 8:
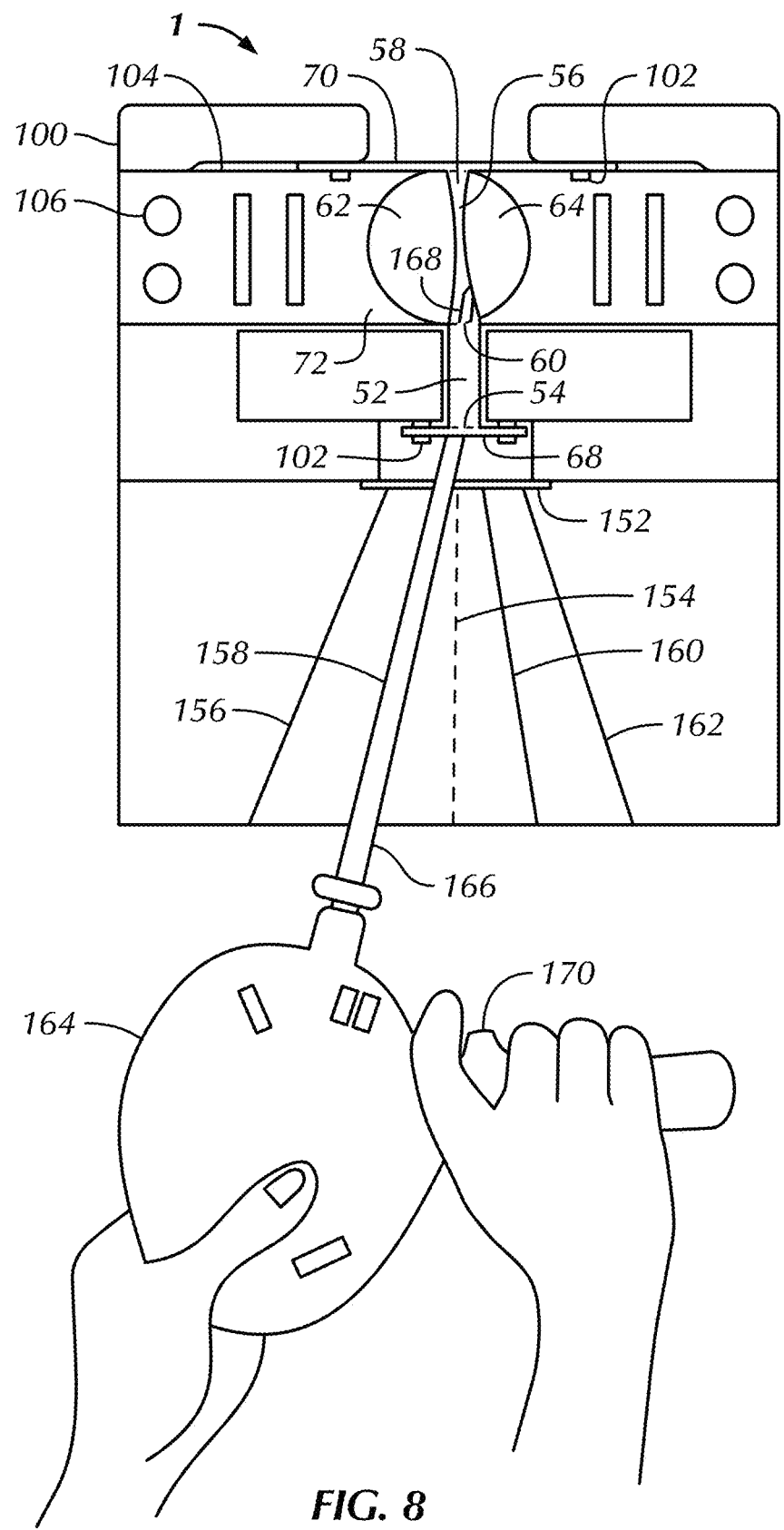
FIG. 8 is a top view, depicting a user using a device for practicing transurethral procedures.

In certain embodiments of simulations using devices disclosed herein, a user begins by positioning an instrument parallel to template 150 in alignment with the guideline that relates to the procedure the user wants to practice. An example instrument insertion using device 1 is shown in FIG. 8. Here, an instrument includes elongate member 166, instrument body 164, and handle assembly 170. Elongate member 166 can be inserted through opening 54 and advanced through duct 52 and opening 60 to localize to lumen 56 with access to lobe 62 and lobe 64. The distal tip 168 of elongate member 166 can be visualized in lumen 56 because lumen 56 is an open lumen.

To practice routine insertion of an instrument into model 50, guideline 154 of template 150 can be used.

Figure 9:
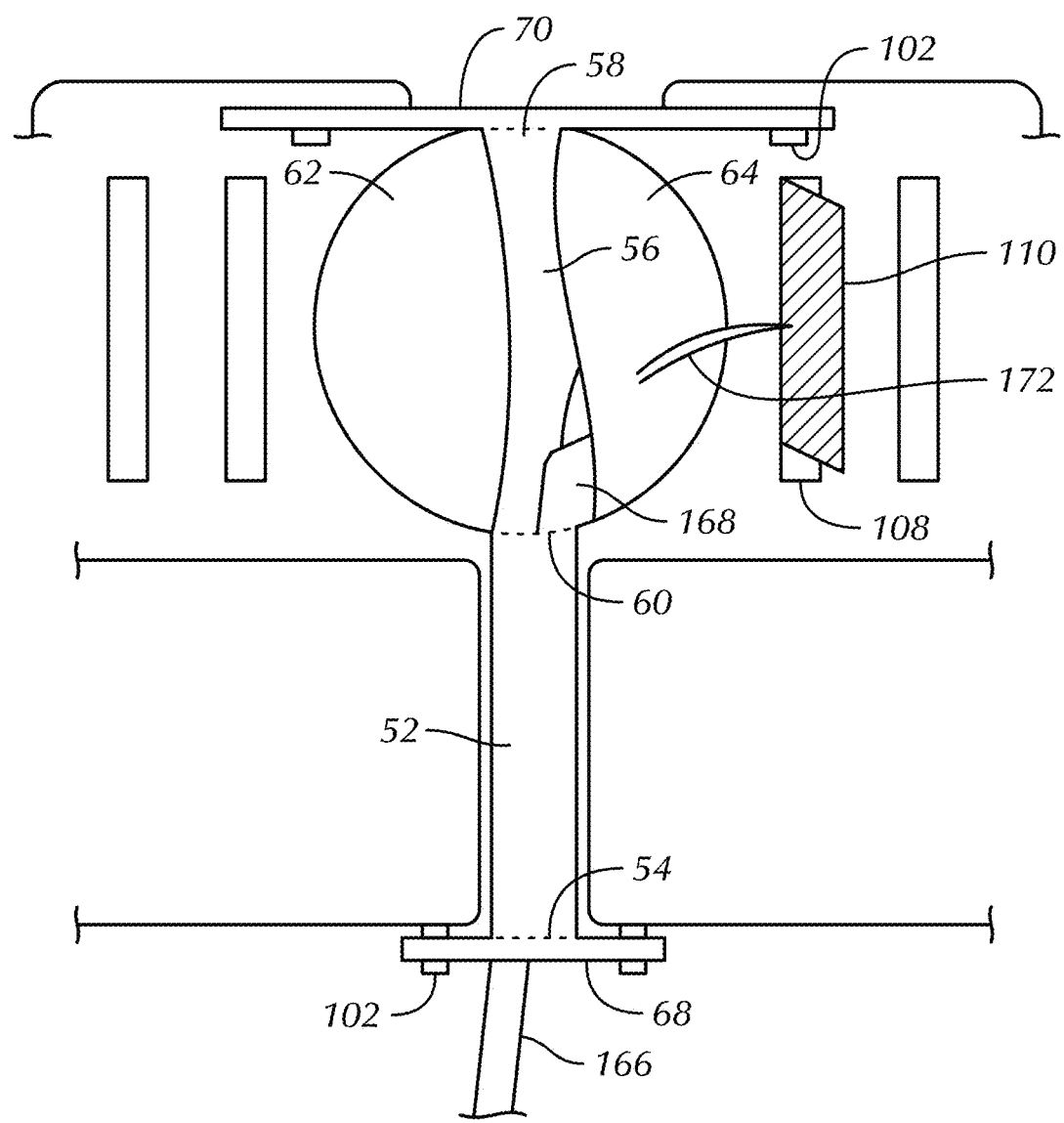
FIG. 9 is a top view, depicting a needle extending from an instrument to penetrate a prostatic lobe of the anatomical model.

Guideline 156 allows a user to learn the angle of entry and instrument deployment at which undesirable bone contact is more likely to occur. In this embodiment, a user places anatomical insert 110 in slot 108 that is directly adjacent to lobe 64. Once distal tip 168 of elongate member 166 is in lumen 56, needle 172 can be extended from tip 168 to penetrate lobe 64 until physical contact is made with anatomical insert 110 as shown in FIG. 9. This simulates the experience of contacting bone during a patient procedure. Guideline 158 can be used to practice manipulation of elongate member 166 to facilitate withdrawal of the instrument.

Guidelines 160 and 162 provide users alternative angles and positions to practice techniques including manipulation of the prostatic capsule, delivery of an implant, and procedures to manage incomplete delivery of an implant. Guidelines 160 and 162 facilitate procedural alignment of an instrument while preventing unwanted contact and damage to surrounding structures. Manipulations of body 72 by an instrument can include cutting, piercing, penetrating, ablating, removing, excising, remodeling, reshaping, or combinations thereof.

Figure 10:
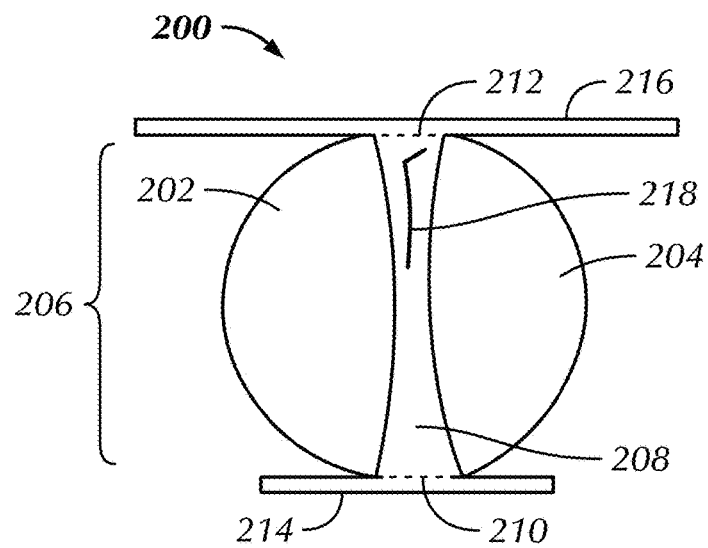
FIG. 10 is a top view of another embodiment of an anatomical model.

Turning to FIG. 10, an alternative embodiment of an anatomical model is shown. Model 200 includes lumen 208 with opening 210 and opening 212 (indicated by dashed lines) and body 206. Lumen 208, which represents that prostatic urethra, resides in body 206 and is situated between two structures, lobe 202 and lobe 204, which represent lobes of the prostate. Lumen 208 is partially exposed to allow visualization of the distal end of an instrument as it passes through opening 210 into lumen 208. Inside lumen 208 can be insert 218, which represents the median lobe of the prostate. Insert 218 can be various lengths and shapes and can be situated at different points along the length of lumen 208. In this alternative embodiment, the anatomical model is constructed such that there is no simulated duct, representing the urethra downstream from the prostatic urethra. Such a configuration allows for various aspects of procedural training to be more easily visualized and communicated.

Model 200 also includes two attachment pieces configured at opposite ends of lumen 208, attachment piece 214 which shares opening 210 and attachment piece 216 which shares opening 212.

Figure 11:
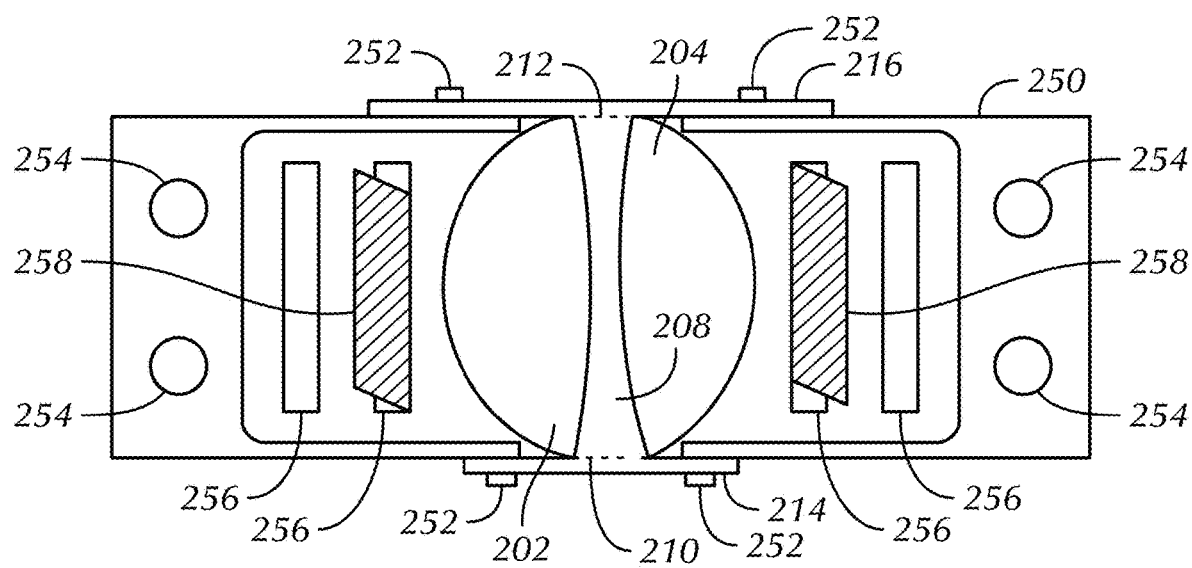
FIG. 11 is a top view of another embodiment of a holder for an anatomical model.

An alternative embodiment of a holder for model 200 is shown in FIG. 11. Holder 250 is designed to allow access by an instrument to opening 210 and opening 212 of model 200. Holder 250 has pegs 252 that fit through holes (not shown) of attachment piece 214 and attachment piece 216 to hold model 200 in place. Model 200 can be further secured by a clear cover (not shown) that lays over body 206. In some embodiments, the cover attaches to holder 250 by magnets 254. Holder 250 can further include slots 256 that are configured to hold rigid inserts 258.

Embodiments of device 1 can use model 200, holder 250 and template 150 to practice transurethral procedures as described above. In these embodiments, an instrument is inserted into opening 210 and advanced within lumen 208 of model 200.

At least one embodiment of the invention includes a device comprising an anatomical model representing the anatomical structure of a human urethra and prostate. The model includes a first opening and a first lumen through which an instrument can be inserted and advanced to a desired location and an indicator apparatus that provides an indication on how to insert and manipulate an instrument in such a manner that prevents unwanted contact and damage to surrounding structures.

In another embodiment of the invention, the indicator apparatus comprises a template that when aligned with the anatomical model defines insertional and procedural angles and positions for an instrument that prevent unwanted contact and damage to surrounding structures.

In another embodiment of the invention, the insertional and procedural angles and positions are defined by lines, figures, symbols or other physical markings on the template.

In another embodiment of the invention, the template includes procedural angles and positions for recovery of an instrument after insertion.

In another embodiment of the invention, the anatomical structures are representative of normal anatomical variations.

In another embodiment of the invention, the anatomical structures are representative of a physiologically normal or healthy male.

In another embodiment of the invention, the anatomical structures are representative of various male reproductive pathologies.

In another embodiment of the invention, the anatomical structures are formed from a flexible material.

In another embodiment of the invention, the first lumen is partially exposed allowing for visualization of the distal end of an instrument.

In another embodiment of the invention, the model includes a second opening and a second lumen through which an instrument can be inserted, wherein the second lumen is enclosed.

In another embodiment of the invention, the second lumen is continuous with the first lumen.

In another embodiment of the invention, the device includes a holder, wherein the holder allows access by an instrument to the first opening of the device.

In another embodiment of the invention, the holder further comprises an anatomical insert.

In another embodiment of the invention, the template can be aligned with the holder such that a user can insert, guide and manipulate an instrument in the device using the insertional and procedural angles and positions indicated on the template.

In another embodiment of the invention, the device is used to practice transurethral access and entry to the prostate using an instrument.

Another embodiment of the invention includes a method for practicing transurethral entry into the prostate and the method can include using an indicator apparatus that provides an indication of how to insert and manipulate an instrument in the urethra to prevent unwanted contact and damage to surrounding structures.

An embodiment of the method for practicing transurethral entry into the prostate can include inserting an instrument as directed by the indicator apparatus into an anatomical model representing the anatomical structure of a human urethra and prostate, wherein the anatomical model is secured to a holder and the holder has an anatomical insert.

An embodiment of the method for practicing transurethral entry into the prostate can include manipulating the instrument after insertion as directed by the indicator apparatus to prevent unwanted contact and damage to surrounding structures.

An embodiment of the method for practicing transurethral entry into the prostate can include that the indicator apparatus comprises a template that when aligned with an anatomical model defines insertional and procedural angles and positions for an instrument that prevent unwanted contact and damage to surrounding structures.

An embodiment of the method for practicing transurethral entry into the prostate can include that the insertional and procedural angles and positions are defined by lines, figures, symbols or other physical markings on the template.

An embodiment of the method for practicing transurethral entry into the prostate can include that the instrument includes an elongate member and a needle advanceable from the elongate member and the needle can be advanced to penetrate the anatomical model and establish contact with the anatomical insert.

An embodiment of the method for practicing transurethral entry into the prostate can include retracting the needle and using the angles and positions of the template to manipulate recovery of the instrument.

An embodiment of the method for practicing transurethral entry into the prostate can include that manipulating the instrument after insertion includes cutting, piercing, penetrating, ablating, removing, excising, remodeling and/or reshaping the anatomical model.

While particular elements, embodiments and applications of the present invention have been shown and described, it will be understood that the invention is not limited thereto since modifications can be made by those skilled in the art without departing from the scope of the present disclosure, particularly in light of the foregoing teachings.

We claim:

1. A device comprising:
   an anatomical model configured to represent the anatomical structure of a human urethra and prostate;

a first opening and a first lumen in the model through which an instrument can be inserted and advanced to a desired location; and an indicator apparatus comprising a template that defines at least one of insertional angles, procedural angles, insertional positions, and procedural positions for the instrument.

2. The device of claim 1, wherein the insertional angles, procedural angles, insertional positions, and procedural positions are defined by lines, figures, symbols or other physical markings on the template.

3. The device of claim 1, wherein the anatomical structures are configured to represent normal human anatomical variations.

4. The device of claim 1, wherein the anatomical structures are configured to represent various male reproductive pathologies.

5. The device of claim 1, wherein the anatomical structures are formed from a flexible material.

6. The device of claim 1, wherein the first lumen is partially exposed such that the distal end of the instrument can be visualized.

7. The device of claim 1, further comprising a second opening and a second lumen through which the instrument can be inserted, wherein the second lumen is enclosed.

8. The device of claim 7, wherein the second lumen is continuous with the first lumen.

9. The device of claim 1, further comprising a holder for the device, wherein the holder is configured to allow access by the instrument to the first opening of the device.

10. The device of claim 9, wherein the holder further comprises an anatomical insert.

11. The device of claim 9, wherein the template can be aligned with the holder such that a user can manipulate the instrument in the device using the insertional angles, procedural angles, insertional positions, or procedural positions indicated on the template.

12. The device of claim 1, wherein the template defines an insertional angle for the instrument.

13. The device of claim 1, wherein the template defines a procedural angle for the instrument.

14. The device of claim 1, wherein the template defines an insertional position for the instrument.

15. The device of claim 1, wherein the template defines a procedural position for the instrument.

16. A method for practicing transurethral entry into a prostate, comprising:

providing an anatomical model configured to represent the anatomical structure of a human urethra, prostate, and surrounding structures;

using an indicator apparatus configured to indicate how to insert and manipulate an instrument in a urethra to prevent unwanted contact and damage to surrounding structures;

inserting the instrument as directed by the indicator apparatus into the anatomical model, wherein the anatomical model is secured to a holder and the holder has an anatomical insert; and manipulating the instrument after insertion as directed by the indicator apparatus to prevent unwanted contact and damage to surrounding structures.

17. The method of claim 16, wherein the indicator apparatus comprises a template that when aligned with an anatomical model defines at least one of insertional angles, procedural angles, insertional positions, or procedural positions for the instrument.

18. The method of claim 17, wherein the insertional angles, procedural angles, insertional positions, or procedural positions are defined by lines, figures, symbols or other physical markings on the template.

19. The method of claim 16, wherein the instrument includes an elongate member and a needle advanceable from the elongate member and the needle can be advanced to penetrate the anatomical model and establish contact with the anatomical insert.

20. The method of claim 16, wherein manipulating the instrument after insertion includes cutting, piercing, penetrating, ablating, removing, excising, remodeling and/or reshaping the anatomical model.

* * * * *